(12) United States Patent
Doan et al.

(10) Patent No.: US 8,831,740 B2
(45) Date of Patent: Sep. 9, 2014

(54) IMPLANTABLE LEAD ASSEMBLY HAVING A PLURALITY OF INDUCTORS

(75) Inventors: Phong D. Doan, Stevenson Ranch, CA (US); Xiaoyi Min, Thousand Oaks, CA (US); Virote Indravudh, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 819 days.

(21) Appl. No.: 12/917,859

(22) Filed: Nov. 2, 2010

(65) Prior Publication Data

US 2012/0109273 A1    May 3, 2012

(51) Int. Cl.
| A61N 1/00 | (2006.01) |
| H01F 27/28 | (2006.01) |
| A61N 1/05 | (2006.01) |
| H01F 5/02 | (2006.01) |
| A61N 1/08 | (2006.01) |

(52) U.S. Cl.
CPC ... *H01F 5/02* (2013.01); *A61N 1/00* (2013.01); *H01F 27/2823* (2013.01); *A61N 2001/086* (2013.01); *A61N 1/05* (2013.01)
USPC ............................................. 607/116

(58) Field of Classification Search
CPC ............ A61N 1/00; A61N 1/02; A61N 1/08; A61N 1/025; A61N 1/32; A61N 1/372
See application file for complete search history.

(56) References Cited

U.S. PATENT DOCUMENTS

| 5,217,010 | A | 6/1993 | Tsitlik et al. |
| 7,013,180 | B2 | 3/2006 | Villaseca et al. |
| 2003/0050557 | A1 | 3/2003 | Susil et al. |
| 2005/0222656 | A1 | 10/2005 | Wahlstrand et al. |
| 2005/0222659 | A1 | 10/2005 | Olsen et al. |
| 2006/0247684 | A1 | 11/2006 | Halperin et al. |
| 2006/0252314 | A1 | 11/2006 | Atalar et al. |
| 2007/0093142 | A1 | 4/2007 | MacDonald et al. |
| 2007/0112398 | A1 | 5/2007 | Stevenson et al. |
| 2007/0255377 | A1 | 11/2007 | Marshall et al. |
| 2008/0033497 | A1 | 2/2008 | Bulkes et al. |
| 2008/0049376 | A1 | 2/2008 | Stevenson et al. |
| 2010/0114276 | A1 | 5/2010 | Min et al. |
| 2010/0114277 | A1 | 5/2010 | Zhao et al. |
| 2010/0138192 | A1 | 6/2010 | Min |
| 2011/0301676 | A1* | 12/2011 | Zhang et al. ................. 607/116 |

* cited by examiner

*Primary Examiner* — Christopher D Koharski
*Assistant Examiner* — Elizabeth K So

(57) ABSTRACT

An implantable lead assembly includes an elongated body, a bobbin, and a conductor. The elongated body includes a distal end having an electrode and a proximal end having a header connector portion for coupling the elongated body with an implantable medical device. The bobbin is disposed in the elongated body. The conductor is disposed in the elongated body and is electrically coupled with the header connector portion and the electrode. The conductor is wound around the bobbin to form first and second inductive coils that are axially separated from each other by an inter-coil gap formed from the bobbin. The first and second inductive coils have different self resonant frequencies.

19 Claims, 6 Drawing Sheets

IMPLANTABLE LEAD ASSEMBLY HAVING A PLURALITY OF INDUCTORS

FIELD OF THE INVENTION

One or more embodiments of the subject matter described herein generally relate to lead assemblies of implantable medical devices that are compatible with magnetic resonance imaging (MRI) systems.

BACKGROUND OF THE INVENTION

Some known implantable lead assemblies that are used with implantable pulse generators (such as neurostimulators, pacemakers, defibrillators, or implantable cardioverter defibrillators (ICD)) are prone to heating and induced current when placed in the strong static, gradient, and/or radiofrequency (RF) magnetic fields of a magnetic resonance imaging (MRI) system. The heating and induced current are the results of the lead assemblies acting as antennas in the magnetic fields generated during a MRI scan. Heating and induced current in the lead assemblies may result in deterioration of stimulation thresholds or, in the context of a cardiac lead, even increase the risk of cardiac tissue damage and perforation.

Many patients with an implantable pulse generator and implanted lead assembly may require, or can benefit from, a MRI scan in the diagnosis or treatment of a medical condition. MRI modality allows for flow visualization, characterization of vulnerable plaque, non-invasive angiography, assessment of ischemia and tissue perfusion, and a host of other applications. The diagnosis and treatment options enhanced by MRI may continue to increase over time. For example, MRI scans have been proposed as a visualization mechanism for lead implantation procedures.

Some known lead assemblies include inductive coils that reduce the induced current within the assemblies when exposed to different external magnetic fields. For example, the lead assemblies may include two coils that are designed to reduce induced current when the lead assemblies are exposed to different magnetic fields. The coils may be relatively close to each other such that the coils may be magnetically coupled. The magnetic coupling of the coils negatively impacts the efficacy of the coils in reducing induced current.

In order to reduce the magnetic coupling of the coils, some known lead assemblies include integrated circuits that are electrically coupled with the coils. The integrated circuits use various techniques to reduce the magnetic coupling between the coils. However, the integrated circuits increase the cost of manufacturing the lead assemblies and increase the size required for the lead assemblies. As a result, the lead assemblies may not be appropriately sized for certain applications, such as the use of the lead assemblies for the treatment of bradycardias. For example, the lead assemblies may be too large and unable to be used as brady leads.

BRIEF SUMMARY OF THE INVENTION

An implantable lead assembly is disclosed herein. In one embodiment, the lead assembly includes an elongated body, a bobbin, and a conductor. The elongated body includes a distal end having an electrode and a proximal end having a header connector portion for coupling the elongated body with an implantable medical device. The bobbin is disposed in the elongated body. The conductor is disposed in the elongated body and is electrically coupled with the header connector portion and the electrode. The conductor is wound around the bobbin to form first and second inductive coils that are axially separated from each other by an inter-coil gap formed from the bobbin. The first and second inductive coils have different self resonant frequencies.

In one aspect, the bobbin includes a plurality of radial indentations with each of the first and second coils of the conductor disposed in a different radial indentation. The bobbin may radially protrude away from a center axis of the elongated body between the first and second coils to fill the inter-coil gap. The first coil of the conductor may have a self resonant frequency range that is generally centered at 64 megahertz while the second coil of the conductor has a self resonant frequency range that is generally centered at 128 megahertz.

In another embodiment, another implantable lead assembly is provided. The lead assembly includes an elongated body, a bobbin, and a conductor. The elongated body includes a distal end having an electrode and a proximal end having a header connector portion configured to be coupled with an implantable medical device. The bobbin is disposed in the elongated body and includes radial indentations that are axially separated from each other by an inter-coil gap. The conductor extends through the elongated body and is electrically coupled with the header connector portion and the electrode. The conductor is wound around the bobbin in the radial indentations to form first and second inductive coils having different self resonant frequencies and separated from each other by the inter-coil gap.

In another embodiment, another implantable lead assembly is provided. The lead assembly includes an elongated body, a bobbin, and a conductor. The elongated body extends along a center axis from a distal end having an electrode to a proximal end having a header connector portion that is configured to be coupled with an implantable medical device. The bobbin is disposed in the elongated body. The conductor extends through the elongated body and is electrically coupled with the header connector portion and the electrode. The conductor is wound around the bobbin to form first and second inductive coils having different self resonant frequencies and separated from each other by an inter-coil gap. The bobbin radially protrudes away from the center axis of the body in the inter-coil gap.

In another embodiment, a method for providing a lead assembly is provided. The method includes providing a conductive pathway that is electrically coupled with an electrode of the lead assembly. The conductive pathway is configured to at least one of sense electrical activity or deliver stimulus pulses using an implantable medical device. The method also includes arranging the conductive pathway within the lead assembly to have a multi-response self resonant frequency (SRF) complex composed of separate, non-overlapping frequency response curves. The frequency response curves are representative of electrical impedance characteristics of the conductive pathway when the conductive pathway is exposed to external magnetic fields of different frequencies.

While multiple embodiments are disclosed, still other embodiments of the described subject matter will become apparent to those skilled in the art from the following Detailed Description, which shows and describes illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

DETAILED DESCRIPTION

One or more embodiments described herein provide an implantable medical lead assembly that includes a conductor wound into a plurality of spaced apart coils. The coils form inductive elements that block the flow of electric current that is induced in the conductor when the lead assembly is exposed to an external magnetic field, such as a magnetic field formed by a magnetic resonance imaging (MRI) system. The conductor is wound in different winding configurations to form the several coils. The coils have different self resonant frequencies (SRF) or ranges of SRF. The conductor has a relatively small gauge and the coils are spaced apart sufficiently far to reduce magnetic coupling between the coils so that the SRF of the coils are separate and independent of each other. As a result, the conductor provides multiple inductive elements having SRF capable of preventing the flow of induced current from different external magnetic fields, such as 1.5 Tesla (T) and 3.0 T fields, to electrodes that are joined to the conductor. The winding configurations of the conductor allow the conductor to be enclosed in relatively small lead assemblies, such as leads used to treat tachycardia (referred to as "tachy leads").

Figure 1:
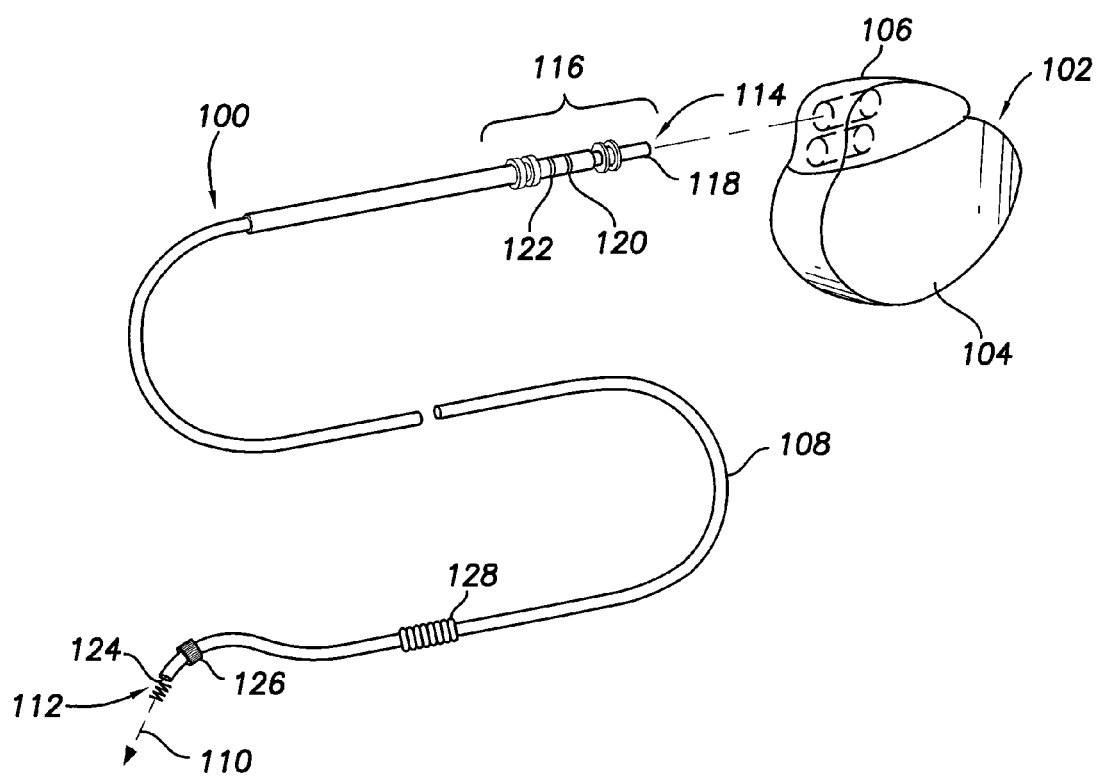
FIG. 1 is a perspective view of one embodiment of a medical implantable lead assembly joined to an implantable medical device (IMD).

FIG. 1 is a perspective view of one embodiment of a medical implantable lead assembly 100 joined to an implantable medical device (IMD) 102. The lead assembly 100 is partially implanted into a heart of a patient to deliver stimulus pulses (such as pacing or defibrillation pulses) to the heart and/or sense cardiac signals of the heart. The IMD 102 generates the stimulus pulses and/or includes a processor to analyze the cardiac signals. The IMD 102 may be a pacemaker, defibrillator, implantable cardiac defibrillator (ICD), or neurostimulator. The IMD 102 includes a housing 104 (also referred to as a "CAN"). The electrical components of the IMD 102 are disposed within the housing 104. The housing 104 includes a header 106 that receives the lead assembly 100.

The lead assembly 100 includes an elongated tubular body 108 extending along a center axis 110 from a distal end 112 to a proximal end 114. As shown in FIG. 1, the center axis 110 may include twists, turns, or undulations, and generally extend along a non-linear path. In one embodiment, the lead assembly 100 is a tachy lead, such as a Riata™ model lead manufactured by St. Jude Medical of St. Paul, Minn. In another embodiment, the lead assembly 100 is a different type, size, or model of a lead.

The proximal end 114 of the lead assembly 100 includes a header connector portion 116. The header connector portion 116 includes several conductive elements, such as a pin contact 118 and ring contacts 120, 122. The number and arrangement of conductive elements in the header connector portion 116 is provided merely as an example and is not intended to be limiting on all embodiments described herein. The header connector portion 116 is received in the header 106 of the IMD 102 such that the contacts 118, 120, 122 engage conductive terminals within the header 106.

The distal end 112 of the lead assembly 100 includes a tip electrode 124 and a ring electrode 126. The tip electrode 124 is shown as an active fixation element, such as a helical anchor that is rotated into cardiac tissue to secure the distal end 112 to the heart. Alternatively, the tip electrode 124 may be a rounded body that is not rotated into or otherwise secured into the cardiac tissue. The ring electrode 126 extends around the outer circumference of the body 108 and is located proximal of the tip electrode 124. In the illustrated embodiment, the lead assembly 100 includes a defibrillation coil electrode 128 disposed about the outer circumference of the body 108. The defibrillation coil electrode 128 is located proximal to the ring electrode 126. The electrodes 124, 126, 128 are electrically coupled with the contacts 118, 120, 122 of the header connector portion 116 of the lead assembly 100. The number, type, and/or arrangement of the electrodes 124, 126, 128 may be different from the embodiment shown in FIG. 1.

Figure 2:
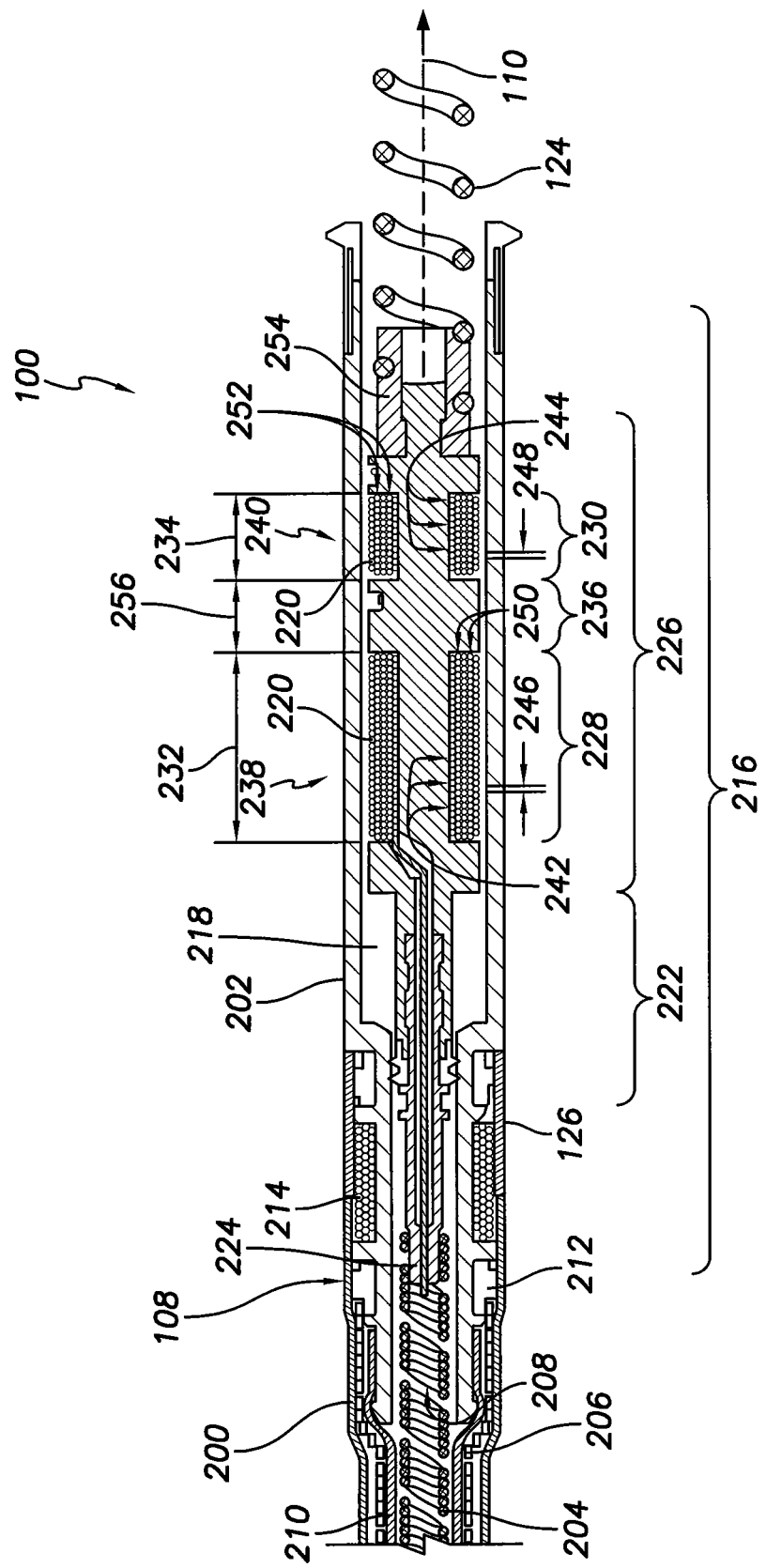
FIG. 2 is a longitudinal cross-sectional view of one embodiment of a distal portion of a lead assembly shown in FIG. 1.

One or more conductors, such as conductors 204, 206 shown in FIG. 2, provide separate electrically conductive pathways between the electrodes 124, 126, 128 and the contacts 118, 120, 122. The conductors convey stimulus pulses from the IMD 102 to one or more of the electrodes 124, 126, 128 and/or convey sensed cardiac signals from the electrodes 124, 126, 128 to the IMD 102.

FIG. 2 is a longitudinal cross-sectional view of one embodiment of a distal portion of the lead assembly 100 shown in FIG. 1. The body 108 of the lead assembly 100 includes an outer tubing 200 joined with a header subassembly 202. The tip electrode 124 is disposed in the header subassembly 202 and may project from and retract into the header subassembly 202. The outer tubing 200 may be formed of a biocompatible electrical insulation material such as, for example, silicone rubber, silicone rubber polyurethane copolymer ("SPC"), polyurethane, or a Gore™ material. The outer tubing 200 may serve as the outer jacket of the body 108 that defines the outer circumferential surface of the body 108.

In the illustrated embodiment, inner and outer coiled conductors 204, 206 (also referred to as first and second coiled conductors 204, 206) extend through the outer tubing 200 of the body 108. The inner and outer conductors 204, 206 are helically wrapped around the center axis 110 of the lead assembly 100. As shown in FIG. 2, the inner and outer conductors 204, 206 form concentric layers of the body 108. The inner conductor 204 defines a central lumen 208 for receiving a stylet or guidewire therethrough. The inner and outer coiled conductors 204, 206 may be separately joined to one or more of the contacts 118, 120, 122 (shown in FIG. 1).

The inner and outer conductors 204, 206 are separated by an inner tubing 210. For example, the inner conductor 204 is disposed within the inner tubing 210 while the outer conductor 206 is disposed outside of the inner tubing 210. In one embodiment, the inner tubing 210 is formed of an electrical insulation material such as, for example, polytetrafluoroethylene (PTFE), ethylene tetrafluoroethylene (ETFE), silicone rubber, or silicone rubber polyurethane copolymer (SPC). The inner tubing 210 electrically isolates the inner conductor 204 from the outer conductor 206 along at least a portion of the length of the body 108.

In the illustrated embodiment, the ring electrode 126 is disposed between the outer tubing 200 and the header subassembly 202. The outer tubing 200 extends to a proximal edge of the ring electrode 126. The header subassembly 202 extends from a distal edge of the ring electrode 126 on the exterior of the body 130 and extends into the outer tubing 200. The outer conductor 206 may be joined to an intermediate conductive body 212 disposed within the outer tubing 200 on the proximal side of the ring electrode 126. A third coiled conductor 214 is joined to the intermediate conductive body 212 such that the third coiled conductor 214 is electrically coupled with the outer conductor 206. The third coiled conductor 214 is a conductive body, such as a wire, filar, or group of wires or filars, that is wrapped around the center axis 110. The coiled conductor 214 is electrically coupled with the ring electrode 126 to electrically couple the ring electrode 126 with one or more of the contacts 118, 120, 122 (shown in FIG. 1) of the header connector portion 116 (shown in FIG. 1) of the lead assembly 100.

The third coiled conductor 214 have an ethylene tetrafluoroethylene (ETFE) insulation layer of 0.5 mils (or 0.01 millimeters). Alternatively, the insulation layer that surrounds the proximal and distal inductive coils 238, 240 may be formed of a different polymer material such as, for example, polytetrafluoroethylene (PTFE), perfluoroalkoxy copolymer resin (PFA), polyimide, or polyurethane.

The third coiled conductor 214 may have a winding configuration that is defined by a number of turns and/or a number of layers of turns. The number of turns can represent the number of times that the third coiled conductor 214 is wrapped around the center axis 110 within a unit length. Alternatively, the number of turns can represent the total number of times that the third coiled conductor 214 is wrapped around the center axis 110. The number of layers represents the number of concentric layers formed by the coils of the third coiled conductor 214. In the illustrated embodiment, the third coiled conductor 214 has three layers with the outer and inner layers having fourteen turns and the middle layer having nineteen turns. Alternatively, the third coiled conductor 214 may have a different winding configuration.

The winding configuration of the third coiled conductor 214 causes the third coiled conductor 214 to be an electrical inductive element in a circuit that includes the ring electrode 126, the third coiled conductor 214, and the outer conductor 206. For example, when exposed to a relatively strong external magnetic field, such as a magnetic field generated by an MRI system, the third coiled conductor 214 may have a relatively large electrical impedance characteristic at one or more frequencies, at an SRF of the third coiled conductor 214, or within a range of SRFs of the third coiled conductor 214. The impedance characteristic can prevent the electric current that is induced by the magnetic field of the MRI system from flowing to the ring electrode 126. The impedance characteristic may increase when the third coiled conductor 214 is exposed to an external magnetic field having a frequency that is equal to or approximately equal to the SRF or is within the range of SRFs of the third coiled conductor 214. As a result, the SRF of the third coiled conductor 214 causes the impedance of the third coiled conductor 214 to increase when exposed to an external magnetic field having the same or similar frequency as the SRF. One or more aspects of the winding configuration can be changed to adjust the SRF of the third coiled conductor 214.

In one embodiment, the lead assembly 100 includes an inductive subassembly 216 that is at least partially disposed in the header subassembly 202. As described below, the inductive subassembly 216 provides electrically inductive elements in a circuit that includes the tip electrode 124. The inductive elements provided by the inductive subassembly 216 are tuned to have separate and distinct SRFs or separate and distinct ranges of SRFs. The separate and distinct SRFs of the inductive subassembly 216 may be tuned to the external magnetic fields generated by MRI systems. For example, the inductive subassembly 216 may have an electrical impedance characteristic that increases when the inductive subassembly 216 is exposed to external magnetic fields having frequencies that are the same as one or more of the SRFs of the inductive subassembly 216.

Figure 3:
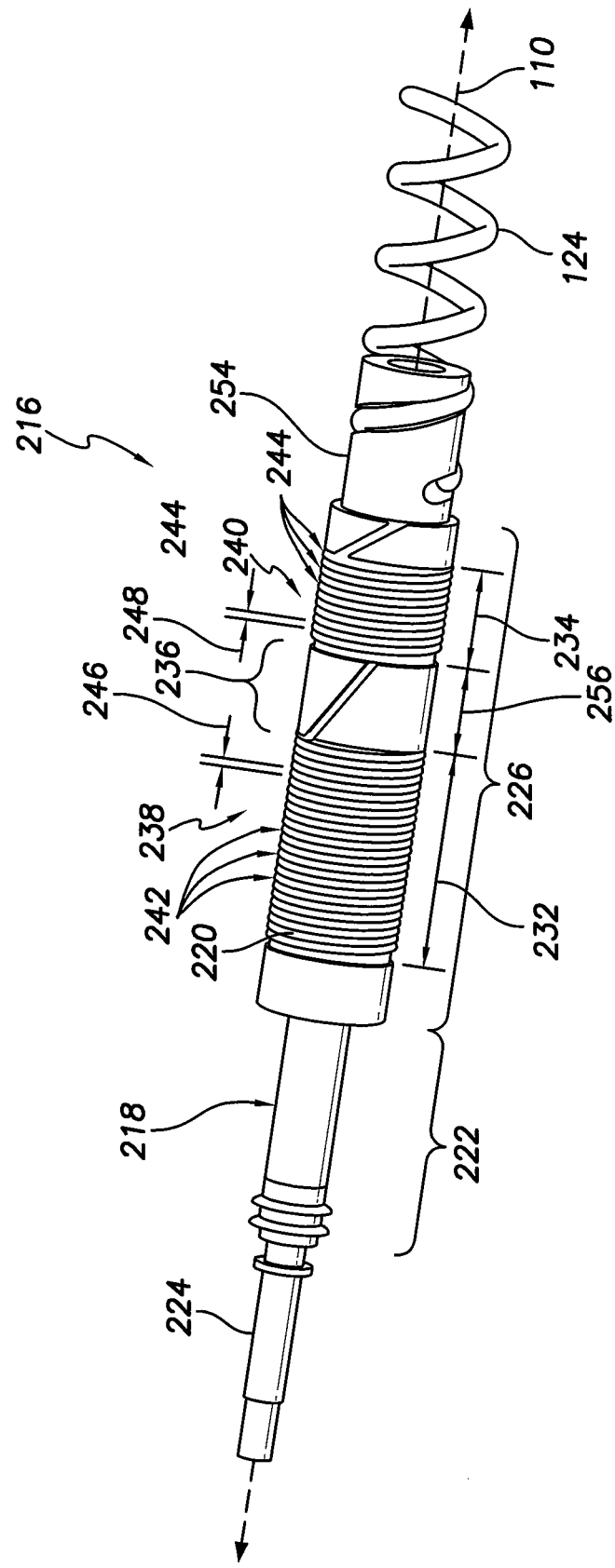
FIG. 3 is a perspective view of one embodiment of an inductive subassembly shown in FIG. 2.

With continued reference to FIG. 2, FIG. 3 is a perspective view of one embodiment of the inductive subassembly 216 shown in FIG. 2. The inductive subassembly 216 includes a bobbin 218 and a fourth coiled conductor 220. The bobbin 218 is a substantially cylindrical body that is elongated along the center axis 110. In the illustrated embodiment, the bobbin 218 has a proximal end 222 that receives a coupler component 224 to mechanically join the bobbin 218 and the coupler component 224. The bobbin 218 may be formed of an electrical insulation material such as PEEK or polyurethane.

The coupler component 224 includes, or is formed from, a conductive material, such as a metal or metal alloy. For example, the coupler component 224 may be formed from a nickel-cobalt-chromium-molybdenum alloy (such as MP35N), platinum, platinum iridium alloy, or stainless steel. As shown in FIG. 2, the inner coiled conductor 204 is joined to the coupler component 224 such that the inner coiled conductor 204 is electrically coupled with the coupler component 224. The fourth coiled conductor 220 is electrically coupled with and extends through the coupler component 224 along the center axis 110.

The bobbin 218 includes a barrel portion 226 about which the fourth coiled conductor 220 is wound. As shown in FIG. 2, the fourth coiled conductor 220 extends through the bobbin 218 such that the fourth coiled conductor 220 passes through the interior of proximal end 222 of the bobbin 218 to the exterior surface of the barrel portion 226 of the bobbin 218.

As shown in FIG. 2, the barrel portion 226 includes two radial indentations 228, 230. The radial indentations 228, 230 are recesses in the bobbin 218 that radially extend inward toward the center axis 110 from the exterior surface of the bobbin 218. Alternatively, a different number of radial indentations 228, 230 may be provided. The radial indentations 228, 230 axially extend in directions parallel to the center axis 110 by respective axial distances 232, 234. In the illustrated embodiment, the axial distance 232 of the proximal radial indentation 228 is longer than the axial distance 234 of the distal radial indentation 230. By way of example only, the axial distance 232 of the proximal radial indentation 228 may be 84 mils (or 2.1 millimeters) and the axial distance 234 of the distal radial indentation 230 may be 36 mils (or 0.91 millimeters). Alternatively, difference axial distances 232, 234 may be used.

The radial indentations 228, 230 are axially separated from each other by an inter-coil gap 236. In the illustrated embodiment, the bobbin 218 projects away from the center axis 110 in the inter-coil gap 236 so that the inter-coil gap 236 is filled by the bobbin 218. The bobbin 218 may be a single, unitary, and continuous body that extends through the barrel portion 226 and radially projects outward to fill the inter-coil gap 236. Alternatively, another material or component may be placed in the inter-coil gap 236 to fill or substantially fill the same. For example, a nonconductive and/or nonmagnetic material may be placed in the inter-coil gap 236 to separate the radial indentations 228, 230.

In the illustrated embodiment, the inductive subassembly 216 includes two inductive coils 238, 240 that helically wrap around the bobbin 218 within the radial indentations 228, 230. Alternatively, a different number of inductive coils 238, 240 may be provided, the inductive coils 238, 240 may wrap around separate or discrete bobbins 218, and/or the inductive coils 238, 240 may wrap around the bobbin 218 in locations other than the radial indentation 228 and/or 230. The inductive coils 238, 240 may be formed by wrapping the fourth coiled conductor 220 around the bobbin 218 within the radial indentations 228, 230.

The fourth coiled conductor 220 can be a continuous conductive body such that the fourth coiled conductor 220 provides a conductive pathway through the bobbin 218 from a location that is proximal to the bobbin 218 to the tip electrode 124 in one embodiment. Alternatively, the fourth coiled conductor 220 may be formed of two or more connected conductive bodies.

The fourth coiled conductor 220 (and the proximal and distal inductive coils 238, 240) may be formed from one or more conductive bodies having relatively small gauges or outer diameters. In one embodiment, the proximal and distal inductive coils 238, 240 are formed with 44 gauge DFT® wire having an ethylene tetrafluoroethylene (ETFE) insulation layer of 0.5 mils (or 0.01 millimeters). Alternatively, the insulation layer that surrounds the proximal and distal inductive coils 238, 240 may be formed of a different polymer material such as, for example, polytetrafluoroethylene (PTFE), perfluoroalkoxy copolymer resin (PFA), polyimide, or polyurethane.

As shown in FIG. 2, the proximal inductive coil 238 of the fourth coiled conductor 220 can be electrically coupled with the inner coiled conductor 204 by the coupler component 224. The distal inductive coil 240 of the fourth coiled conductor 220 can be electrically coupled with a base 254 of the inductive subassembly 216. The base 254 and the tip electrode 124 are mechanically and electrically coupled with each other. The base 254 includes or is formed from a conductive material, such as platinum, a platinum-iridium alloy, a nickel-cobalt alloy (such as MP35N), or stainless steel, for example. The proximal and distal inductive coils 238, 240 of the fourth coiled conductor 220 provide an electrically conductive pathway extending from coupler component 224 to the base 254 such that stimulus pulses can be conveyed from the inner coiled conductor 204 to the tip electrode 124 via the proximal and distal inductive coils 238, 240 and/or cardiac signals may be conveyed from the tip electrode 124 to the inner coiled conductor 204 via the proximal and distal inductive coils 238, 240.

As shown in FIG. 2, the fourth coiled conductor 220 is a continuous conductive body such that the inductive coils 238, 240 are electrically coupled with each other and provide a conductive pathway that extends from the proximal end 222 of the bobbin 218 and through the length of the barrel portion 226 of the bobbin 218. The inductive coils 238, 240 may be separately referred to as a proximal inductive coil 238 and a distal inductive coil 240.

The inductive coils 238, 240 are designed and arranged within the inductive subassembly 216 to have relatively high impedances at two or more different and separate SRFs while consuming a relatively small amount of space within the lead assembly 100. For example, the inductive coils 238, 240 may each have a different and separate SRF relative to the other inductive coils 238, 240 when exposed to magnetic fields.

Figure 4:
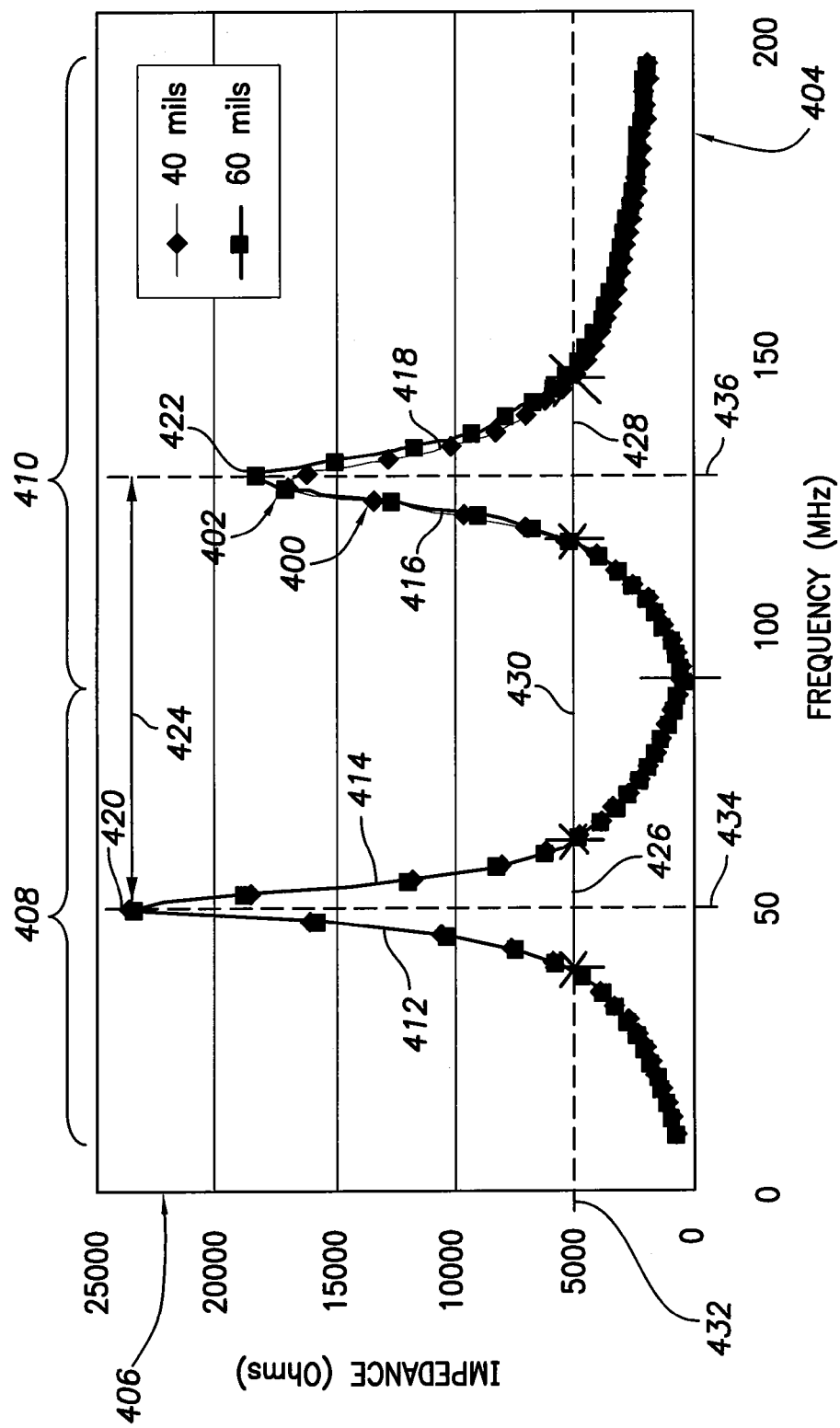
FIG. 4 is an illustration of electrical impedance characteristics of the inductive subassembly shown in FIG. 2 in accordance with one embodiment.

FIG. 4 is an illustration of multi-response SRF complexes 400, 402 of the inductive subassembly 216 (shown in FIG. 2) in accordance with one embodiment. The multi-response SRF complexes 400, 402 are shown alongside a horizontal axis 404 representative of frequency and a vertical axis 406 representative of electrical impedance. The frequencies of the horizontal axis 404 are the frequencies of an external magnetic field to which the inductive subassembly 216 is exposed. The electrical impedances represented by the vertical axis 406 are the electrical impedance characteristics of the inductive subassembly 216 when the inductive subassembly 216 is exposed to magnetic fields of the different frequencies.

The multi-response SRF complexes 400, 402 are frequency responses of the proximal and distal inductive coils 238, 240 (shown in FIG. 2) of the inductive subassembly 216 (shown in FIG. 2). The multi-response SRF complexes 400, 402 represent electrical impedance characteristics of the conductive pathway formed by the proximal and distal inductive coils 238, 240 over a range of frequencies of external magnetic fields, such as RF magnetic fields generated by MRI systems. The multi-response SRF complexes 400, 402 indicate how the electrical inductance of the conductive pathway formed by the proximal and distal inductive coils 238, 240 changes when exposed to different frequencies of the external magnetic field.

The multi-response SRF complexes 400, 402 represent the electrical impedance characteristics of the inductive subassembly 216 (shown in FIG. 2) for different separation distances 256 (shown in FIG. 2) between the proximal and distal inductive coils 238, 240 (shown in FIG. 2). In the illustrated embodiment, the multi-response SRF complex 400 represents the electrical impedance characteristics of the proximal and distal inductive coils 238, 240 when the separation distance 256 is shorter than the separation distance 256 associated with the multi-response SRF complex 402. For example, the multi-response SRF complex 400 may be associated with a separation distance 256 of 40 mils (or 1.0 millimeter) while the multi-response SRF complex 402 is associated with a separation distance 256 of 60 mils (or 1.5 millimeters).

As shown in FIG. 4, the multi-response SRF complexes 400, 402 significantly overlap over the range of frequencies shown along the horizontal axis 404. For example, the multi-response SRF complexes 400, 402 indicate that the electrical impedance characteristics of the conductive pathway formed by the proximal and distal inductive coils 238, 240 (shown in FIG. 2) are approximately the same when the separation distance 256 is 40 to 60 mils (or 1.0 to 1.5 millimeters) over a range of frequencies. The multi-response SRF complexes 400, 402 may continue to be approximately the same over a range of frequencies when the separation distance 256 is varied between 40 and 60 mils (or 1.0 to 1.5 millimeters).

The discussion herein on the features and characteristics of the multi-response SRF complexes 400, 402 focuses on the multi-response SRF complex 400, but may apply equally to the multi-response SRF complex 402. The multi-response SRF complex 400 includes frequency response curves 408, 410. The frequency response curves 408, 410 represent the electrical impedance characteristics of the proximal and distal inductive coils 238, 240 (shown in FIG. 2) in one embodiment. For example, the frequency response curve 408 may represent the electrical impedance characteristics of the proximal inductive coil 238 and the frequency response curve 410 may represent the electrical impedance characteristics of the distal inductive coil 240 along the range of frequencies shown on the horizontal axis 404.

The frequency response curve 408 transitions into the frequency response curve 410 in the illustrated embodiment. Alternatively, the frequency response curves 408, 410 may be separated by a gap. While only two frequency response curves 408, 410 are provided for each multi-response SRF complex 400, 402, alternatively a different number of frequency response curves 408, 410 may be provided for one or more of the multi-response SRF complexes 400, 402.

The frequency response curves 408, 410 include respective rising edges 412, 414, falling edges 416, 418, and center frequencies 434, 436. The center frequencies 434, 436 are disposed between the rising edges 412, 414 and falling edges 416, 418 of each frequency response curve 408, 410. Although referred to as "center" frequencies, the center frequencies 434, 436 may be offset from the exact center of the range of frequencies encompassed by the frequency response curves 408, 410 or portions thereof. In the illustrated embodiment, the center frequencies 434, 436 are located at or near peaks 420, 422 of the frequency response curves 408, 410.

The center frequencies 434, 436 represent relatively large electrical impedance characteristics of the inductive subassembly 216 (shown in FIG. 2) at the corresponding frequencies at or near which the peaks 420, 422 occur. For example, the center frequency 434 represents an electrical impedance characteristic that is greater than the electrical impedance characteristics of the rising and falling edges 412, 414. The center frequency 436 represents an electrical impedance characteristic that is greater than the electrical impedance characteristics of the rising and falling edges 416, 418. While only one center frequency 434, 436 and one peak 420, 422 are shown for each frequency response curve 408, 410, alternatively a different number of center frequencies 434, 436 and/or peaks 420, 422 may be provided for one or more of the frequency response curves 408, 410.

As shown in FIG. 4, the frequency response curves 408, 410 are separate and distinct from each other. The center frequencies 434, 436 are separated from each other by a peak separation spectrum 424. As the peak separation spectrum 424 increases, the center frequencies 434, 436 move farther apart and, as the peak separation spectrum 424 decreases, the center frequencies 434, 436 move closer together. The peak separation spectrum 424 may be based on predetermined frequencies of magnetic fields to which the inductive subassembly 216 (shown in FIG. 2) may be exposed. For example, the location or frequency at which the center frequencies 434, 436 occur may be associated with the frequencies of MRI systems to which the inductive subassembly 216 may be or is likely to be exposed. In the illustrated embodiment, the center frequency 424 is located at or near a frequency of 50 MHz. Alternatively, the center frequency 424 may be located at or near a frequency of 64 MHz. MRI systems that generate 1.5 Tesla magnetic fields may operate at a frequency that is at or near 64 MHz. The location of the center frequency 424 in the frequency response curve 408 can result in increased impedance of the inductive subassembly 216 when the inductive subassembly 216 is exposed to a 1.5 Tesla magnetic field of an MRI system.

The center frequency 426 may be located at or near a frequency of 128 MHz. MRI systems that generate 3.0 Tesla magnetic fields may operate at a frequency that is at or near 128 MHz. The location of the center frequency 426 in the frequency response curve 410 can result in increased impedance of the inductive subassembly 216 when the inductive subassembly 216 is exposed to a 3.0 Tesla magnetic field of an MRI system.

The separation of the frequency response curves 408, 410 along the multi-response SRF complex 400 may be established or identified in a variety of ways. For example, the peak separation spectrum 424 may exceed a predetermined threshold when the frequency response curves 408, 410 are separate and distinct. If the peak separation spectrum 424 does not exceed the predetermined threshold, then the frequency response curves 408, 410 may not be separate and distinct.

Alternatively, the separation of the frequency response curves 408, 410 may be identified when portions of the frequency response curves 408, 410 do not overlap each other. For example, separation of the frequency response curves 408, 410 can exist when the falling edge 414 of the frequency response curve 408 does not overlap or intersect the rising edge 416 of the frequency response curve 410.

Separation can exist when the frequency response curves 408, 410 have non-overlapping bandwidth spectra 426, 428. The bandwidth spectrum 426, 428 of each frequency response curve 408, 410 represents a portion of the frequency response curve 408, 410 between the rising edge 412, 416 and falling edge 414, 418 of the frequency response curve 408, 410. The bandwidth spectra 426, 428 may be identified as the range of frequencies encompassed by the corresponding frequency response curve 408, 410 at or below an impedance threshold 432. For example, in the illustrated embodiment, the bandwidth spectrum 426, 428 of each frequency response curve 408, 410 includes the range of frequencies encompassed by each frequency response curve 408, 410 at the impedance threshold 432 of 5,000 Ohms. Alternatively, a different value for the impedance threshold 432 may be used.

The amount of overlap between the frequency response curves 408, 410 may be characterized by an overlap percentage. The overlap percentage is based on the range of frequencies encompassed by both bandwidth spectra 426, 428 relative to the range of frequencies encompassed by the bandwidth spectrum 426 and/or 428. In the illustrated embodiment, the bandwidth spectra 426, 428 do not overlap, or do not include any common frequencies between the two bandwidth spectra 426, 428. As a result, the overlap percentage is 0%.

For another example, if a first bandwidth spectra extends from 30 MHz to 100 MHz and a second bandwidth spectra extends from 90 MHz to 200 MHz, then first bandwidth spectrum includes a frequency range of 70 MHz, the second bandwidth spectrum includes a frequency range of 110 MHz, and the overlap in frequencies between the first and second bandwidth spectra extends from 90 MHz to 100 MHz, or ranges a total of 10 MHz. In order to calculate the overlap percentage between the first and second bandwidth spectra, the overlap frequency range of 10 MHz is divided by the frequency range of the first bandwidth spectrum (e.g., 70 MHz) and/or the frequency range of the second bandwidth spectrum (e.g., 110 MHz). If the overlap percentage is calculated with reference to the first bandwidth spectrum, then the overlap percentage is approximately 14% (e.g., 10 MHz divided by 70 MHz yields a percentage of approximately 14%). If the overlap percentage is calculated with reference to the second bandwidth spectrum, then the overlap percentage is approximately 9.1% (e.g., 10 MHz divided by 110 MHz yields a percentage of approximately 9.1%). Alternatively, the overlap percentage may be measured as an average, median, deviation, or other statistical measure of the overlap percentages of the bandwidth spectra associated with a plurality of frequency responses.

The frequency response curves 408, 410 may be separate and distinct when the overlap percentage of the frequency response curves 408, 410 is less than a predetermined threshold. For example, the frequency response curves 408, 410 may be separate and distinct when one or more of the overlap percentages associated with the frequency response curves 408, 410 is less than 5%, less than 10%, less than 15%, less than 20%, less than 25%, less than 30%, less than 35%, less than 40%, less than 45%, or less than 50%. Alternatively, the frequency response curves 408, 410 may be separate and distinct when an average, median, deviation, maximum, or other statistical measure of the set of overlap percentages associated with a plurality of frequency responses does not exceed a predetermined threshold.

In another embodiment, separation can exist when the bandwidth spectra 426, 428 of the frequency response curves 408, 410 are separated by at least a threshold range of frequencies. The range of frequencies that extend between the bandwidth spectra 426, 428 may be referred to as a frequency response transition zone 430. The transition zone 430 may be identified as the range of frequencies encompassed from the intersection of the falling edge 414 of the frequency response curve 408 and the impedance threshold 432 to the intersection of the rising edge 416 of the following frequency response curve 410 and the impedance threshold 432. The transition zone 430 shown in FIG. 4 extends from approximately 70 MHz to approximately 120 MHz. The range of frequencies in the transition zone 430 can be referred to as a transition zone frequency range and may be compared to a frequency range threshold to determine if the frequency response curves 408, 410 are distinct and separate. For example, the transition zone frequency range of 50 MHz (e.g., the difference between 70 and 120 MHz) may be compared to a frequency range threshold of 5 MHz, 10 MHz, 15 MHz, 20 MHz, 25 MHz, 30 MHz, 35 MHz, 40 MHz, 45 MHz, 50 MHz, 55 MHz, 60 MHz, 65 MHz, 70 MHz, and the like. If the transition zone frequency range exceeds the frequency range threshold, then the frequency response curves 408, 410 can be identified as separate and distinct from each other. Conversely, if transition zone frequency range does not exceed the frequency range threshold, then the frequency response curves 408, 410 may not be identified as separate and distinct from each other.

Figure 5:
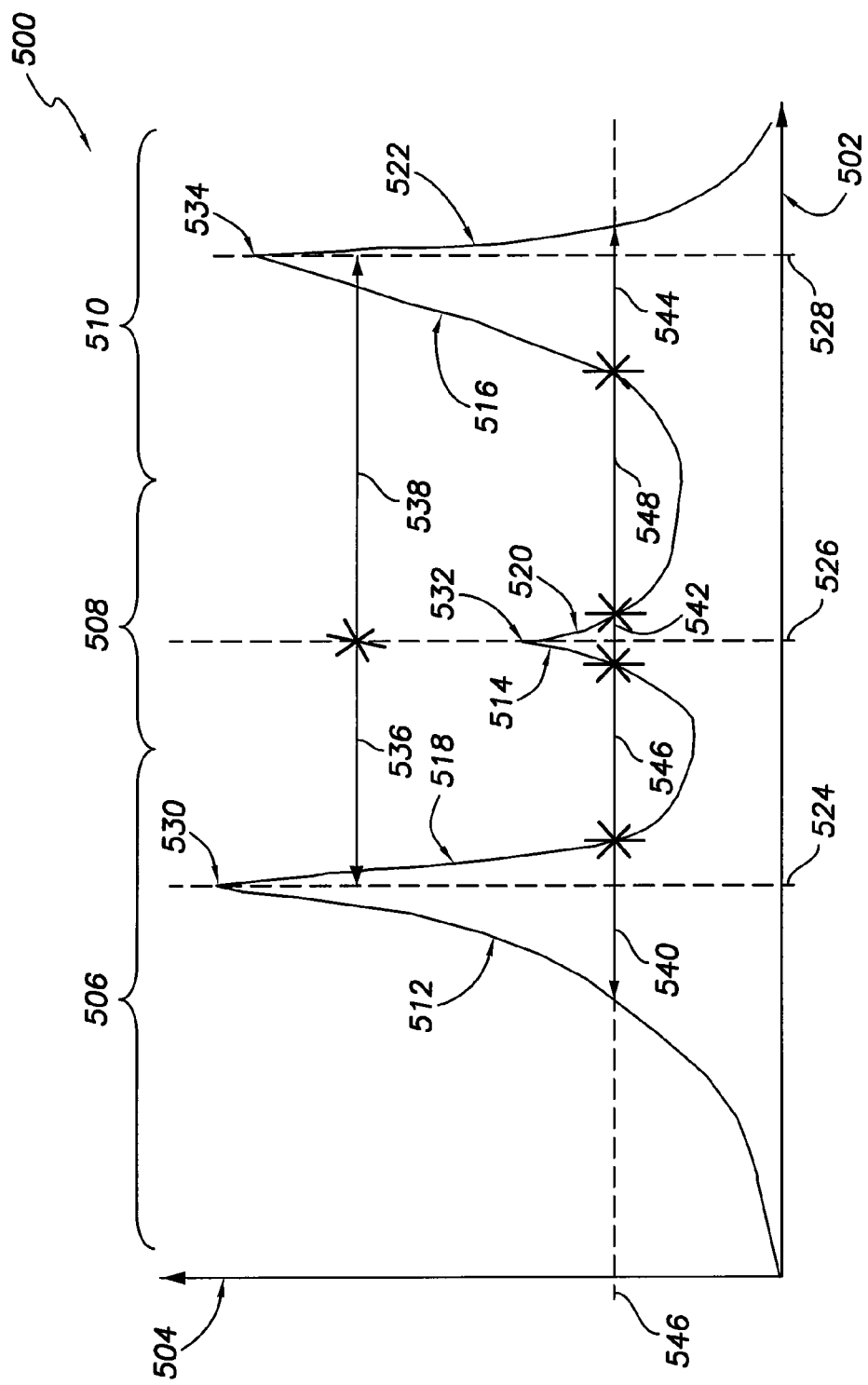
FIG. 5 is an illustration of a multi-response SRF complex of an inductive subassembly in accordance with another embodiment.

FIG. 5 is an illustration of a multi-response SRF complex 500 of an inductive subassembly in accordance with another embodiment. The multi-response SRF complex 500 is shown alongside a horizontal axis 502 representative of frequency and a vertical axis 504 representative of electrical impedance. The frequencies of the horizontal axis 502 are the frequencies of an external magnetic field to which an inductive subassembly of a lead assembly is exposed. The electrical impedances represented by the vertical axis 504 are the electrical impedance characteristics of the inductive subassembly when the inductive subassembly is exposed to magnetic fields of the different frequencies.

The multi-response SRF complex 500 is the frequency response of an inductive subassembly, such as an inductive subassembly having three or more inductive coils. The multi-response SRF complex 500 represents electrical impedance characteristics of one or more conductive pathways formed by several inductive coils or other inductors over a range of frequencies of external magnetic fields, such as RF magnetic fields generated by MRI systems. The multi-response SRF complex 500 indicates how the electrical inductance of the conductive pathway formed by the inductive coils and/or other inductors changes when exposed to different frequencies of the external magnetic field.

In contrast to the multi-response SRF complexes 400, 402 (shown in FIG. 4), the multi-response SRF complex 500 includes three frequency response curves 506, 508, 510. Alternatively, the multi-response SRF complex 500 may include more than three frequency response curves 506, 508, 510. The frequency response curves 506, 508, 510 may represent the electrical impedance characteristics of three inductive coils that are electrically coupled to form a single conductive pathway through an inductive subassembly in one embodiment. Alternatively, the frequency response curves 506, 508, 510 may represent the electrical impedance characteristics of three or more coils and/or other inductive components (such as LC or tank circuits, RLC circuits, and the like) that are electrically coupled with each other.

The frequency response curve 506 transitions into the frequency response curve 508 and the frequency response curve 508 transitions into the frequency response curve 510 in the illustrated embodiment. Alternatively, two more of the neighboring frequency response curves 506, 508, 510 may be separated by a gap.

The frequency response curves 506, 508, 510 include respective rising edges 512, 514, 516, falling edges 518, 520, 522, and center frequencies 524, 526, 528. In the illustrated embodiment, the center frequencies 434, 436 are located at or near peaks 530, 532, 534 of the frequency response curves 506, 508, 510.

As shown in FIG. 5, the frequency response curves 506, 508, 510 are separate and distinct from each other. Neighboring center frequencies 524, 526 and neighboring center frequencies 526, 528 are separated from each other by corresponding peak separation spectra 536, 538. As the peak separation spectrum 536 increases, the neighboring center frequencies 524, 526 move farther apart and, as the peak separation spectrum 536 decreases, the center frequencies 524, 526 move closer together. Similarly, as the peak separation spectrum 538 increases, the neighboring center frequencies 526, 528 move farther apart and, as the peak separation spectrum 538 decreases, the center frequencies 526, 528 move closer together.

The peak separation spectrum 536 and/or 538 may be based on predetermined frequencies of magnetic fields to which the inductive subassembly is exposed. The location or frequency at which the center frequencies 530, 532, 534 occur may be associated with the frequencies of MRI systems to which the inductive subassembly may be or is likely to be exposed. By way of example only, the center frequency 530 may be located at or near 64 MHz, the center frequency 532 may be located at or near 128 MHz, and the center frequency 534 may be located at or near 192 MHz or 256 MHz. Alternatively, one or more of the center frequencies 530, 532, 534 may be located at another frequency.

The separation of the frequency response curves 506, 508, 510 along the multi-response SRF complex 500 may be established or identified in a variety of ways. For example, the peak separation spectrum 536 and/or 538 may exceed predetermined thresholds when the frequency response curves 506, 508 and/or the frequency response curves 508, 510 are separate and distinct. If the peak separation spectrum 536 and/or 538 does not exceed the predetermined threshold, then the frequency response curves 506, 508 and/or the frequency response curves 508, 510 may not be separate and distinct.

Alternatively, the separation of the frequency response curves 506, 508, 510 may be identified when portions of the frequency response curves 506, 508, 510 do not overlap each other. For example, separation of the frequency response curves 506, 508, 510 can exist when the falling edge 518, 520 of the corresponding frequency response curve 506, 508 does not overlap or intersect the rising edge 514, 516 of the subsequent or following frequency response curve 508, 510.

Separation can exist when the frequency response curves 506, 508, 510 have non-overlapping bandwidth spectra 540, 542, 544. The bandwidth spectra 540, 542, 544 may be identified as the range of frequencies encompassed by the corresponding frequency response curve 506, 508, 510 at or below an impedance threshold 546.

The amount of overlap between the frequency response curves 506, 508, 510 may be characterized by the overlap percentage that is based on the bandwidth spectra 540, 542, 544. For example, as described above, the overlap percentage can be calculated based on the range of frequencies encompassed by bandwidth spectra 540, 542, 544 of neighboring frequency responses 506, 508, 510. In the illustrated embodiment, the bandwidth spectra 540, 542, 544 do not overlap, or do not include any common frequencies between any two neighboring bandwidth spectra 540, 542, 544. For example, the bandwidth spectrum 540 does not overlap with the bandwidth spectrum 542 and the bandwidth spectrum 542 does not overlap with the bandwidth spectrum 544.

In another embodiment, separation can exist when the bandwidth spectra 540, 542, 544 of neighboring frequency response curves 506, 508, 510 are separated by at least a threshold range of frequencies. The range of frequencies that extend between the bandwidth spectra 540, 542, 544 of neighboring frequency response curves 506, 508, 510 may be referred to as frequency response transition zones 546, 548. The range of frequencies in each transition zone 546, 548 can be referred to as a transition zone frequency range and may be compared to a frequency range threshold to determine if the frequency response curves 506, 508, 510 are distinct and separate. If the transition zone frequency range between neighboring frequency response curves 506, 508, 510 exceeds the frequency range threshold, then the neighboring frequency response curves 506, 508, 510 can be identified as separate and distinct from each other. Conversely, if transition zone frequency range between neighboring frequency response curves 506, 508, 510 does not exceed the frequency range threshold, then the neighboring frequency response curves 506, 508, 510 may not be identified as separate and distinct from each other.

Returning to the discussion of the inductive subassembly 216 shown in FIG. 3, the inductive coils 238, 240 have the multi-response SRF complexes 400, 402, and/or 500 (shown in FIGS. 4 and 5) due to the different winding configurations of the coils 238, 240. The proximal and distal inductive coils 238, 240 are arranged to prevent the flow of induced currents while taking up sufficiently small space in the lead assembly 100 that the inductive subassembly 216 may be provided in relatively small lead assemblies 100, such as brady lead assemblies, or lead assemblies that are inserted into the heart to treat bradycardia.

The proximal and distal inductive coils 238, 240 have different SRFs or different overlapping or non-overlapping ranges of SRFs in one embodiment. For example, the proximal inductive coil 238 may an SRF of 128 MHz or approximately 128 MHz, or may have a range of SRFs that includes 128 MHz while the distal inductive coil 240 may have an SRF of 64 MHz or approximately 64 MHz, or may have a range of SRFs that includes 64 MHz. Alternatively, the distal inductive coil 240 may have a larger SRF than the proximal inductive coil 238. In another embodiment, the proximal and distal inductive coils 238, 240 may have different SRFs than those described above. The different SRFs of the proximal and distal inductive coils 238, 240 enables the single fourth coiled conductor 220 to prevent flow of electric current that is induced in the fourth coiled conductor 220 by different strengths of MRI systems. For example, the smaller SRF of the distal inductive coil 240 may be smaller than the SRF of the proximal inductive coil 238 such that the distal inductive coil 240 prevents flow of current that is induced by a 1.5 Tesla MRI system while the proximal inductive coil 238 prevents flow of current that is induced by a 3.0 Tesla MRI system. Alternatively, the fourth coiled conductor 220 may include a different number of inductive coils and/or inductive coils that prevent flow of current that is induced by MRI systems of strengths other than 1.5 and/or 3.0 Tesla.

The fourth coiled conductor 220 is helically wrapped around the bobbin 218 in different wrapping configurations to form the proximal and distal inductive coils 238, 240. The wrapping configurations of the proximal and distal inductive coils 238, 240 may be defined by the respective axial distances 232, 234, number of turns, and/or number of layers of the fourth coiled conductor 220. For example, the proximal inductive coil 238 may have a greater axial distance 232 than the axial distance 234 of the distal inductive coil 240, as shown in the illustrated embodiment. Alternatively, the axial distance 232 of the proximal inductive coil 238 may be the same as or smaller than the axial distance 234 of the distal inductive coil 240.

The proximal inductive coil 238 and the distal inductive coil 240 may have different numbers of turns 242, 244. The number of turns 242, 244 of the different proximal and distal inductive coils 238, 240 can represent the total number of times that the fourth coiled conductor 220 is wrapped around the bobbin 218. In the illustrated embodiment, the number of turns 242 for the proximal inductive coil 238 is 28 and the number of turns 244 for the distal inductive coil 240 is 12. Alternatively, the number of turns 242, 244 for the proximal and/or distal inductive coils 238, 240 may be a different number. The number of turns 242, 244 may be based on the axial distance 232, 234 of the radial indentations 228, 230 in which the corresponding proximal and distal inductive coil 238, 240 is disposed. For example, as the axial distance 232 of the radial indentation 228 and the proximal inductive coil 238 increases, the number of turns 242 of the proximal inductive coil 238 may increase to lengthen the proximal inductive coil 238 along the center axis 110. Similarly, as the axial distance 234 of the radial indentation 230 and the distal inductive coil 240 increases, the number of turns 244 of the distal inductive coil 240 may increase to lengthen the distal inductive coil 240 along the center axis 110. Conversely, as the axial distance 232 of the radial indentation 228 and the proximal inductive coil 238 decreases, the number of turns 242 of the proximal inductive coil 238 may decrease to shorten the proximal inductive coil 238 along the center axis 110. As the axial distance 234 of the radial indentation 230 and the distal inductive coil 240 decreases, the number of turns 244 of the distal inductive coil 240 may decrease to shorten the distal inductive coil 240 along the center axis 110.

The winding configurations of the proximal and distal inductive coils 238, 240 may include a pitch distance 246, 248 of the turns 242, 244. The pitch distances 246, 248 represent axial distances, or distances measured in directions parallel to the center axis 110, between common points of adjacent turns 242, 244. For example, the pitch distance 246 may represent the distance along the center axis 110 between center lines of adjacent turns 242 of the coiled conductor 220 in the proximal inductive coil 238. The pitch distance 248 may represent the distance along the center axis 110 between center lines of adjacent turns 244 of the coiled conductor 220 in the distal inductive coil 240. In the illustrated embodiment, the pitch distances 246, 248 are the same or approximately the same. Alternatively, the pitch distances 246, 248 may significantly differ from each other. For example, the pitch distances 246, 248 may differ by 10% or more.

Another aspect of the winding configurations of the proximal and distal inductive coils 238, 240 includes the number of layers 250, 252 of the proximal and distal inductive coils 238, 240. As described above, the number of layers of a coiled conductor such as the fourth coiled conductor 220 represents the number of concentric layers formed by the fourth coiled conductor 220 as the fourth coiled conductor 220 is wrapped around the center axis 110. Multiple layers 250, 252 may be formed when the fourth coiled conductor 220 is wrapped around the bobbin 218 to form a first layer, then wrapped around the first layer to form a second layer, and so on. As shown in FIG. 2, in the illustrated embodiment both the proximal and distal inductive coils 238, 240 have five layers 250, 252. Alternatively, the number of layers 250, 252 may differ from each other. In another embodiment, the proximal and/or distal inductive coils 238, 240 have a different number of layers 250, 252. By way of example only, the proximal and/or distal inductive coils 238, 240 may have three or seven layers 250, 252.

As described above, the proximal and distal inductive coils 238, 240 have different and separate SRFs such that the proximal and distal inductive coils 238, 240 have relatively high electrical impedance characteristics when exposed to different external magnetic fields. By "different" SRFs, it is meant that the proximal and distal inductive coils 238, 240 have relatively high impedances when exposed to different external magnetic fields. For example, when the proximal and distal inductive coils 238, 240 are exposed to a 1.5 Tesla external magnetic field, the proximal inductive coil 238 may have a significantly larger electrical impedance characteristic than the distal inductive coil 240. When the proximal and distal inductive coils 238, 240 are exposed to a 3.0 Tesla external magnetic field, the distal inductive coil 240 may have a significantly larger electrical impedance characteristic than the proximal inductive coil 238. By "independent" SRFs, it is meant that the SRF of the proximal inductive coil 238 is not dependent on the SRF of the distal inductive coil 240, and vice-versa. For example, the winding configuration of the proximal inductive coil 238 may not impact or change the SRF of the distal inductive coil 240 and the winding configuration of the distal inductive coil 240 may not impact or change the SRF of the proximal inductive coil 238. While the embodiments discussed herein are given in the context of being tuned to have SRFs appropriate for 64 MHz and 128 MHz MRI systems (which can produce 1.5 Tesla and 3.0 Tesla external magnetic fields, respectively), the proximal and distal inductive coils 238, 240 could be tuned to have SRFs appropriate for the frequency of another type of MRI system currently existing or yet to be developed.

The SRFs of the proximal and distal inductive coils 238, 240 are separate and independent by magnetically decoupling the proximal and distal inductive coils 238, 240 from each other. In the illustrated embodiment, the proximal and distal inductive coils 238, 240 are magnetically decoupled from each other without including additional magnetic and/or conductive components between the proximal and distal inductive coils 238, 240. For example, as shown in FIGS. 2 and 3, no magnetic and/or conductive materials are provided between the proximal and distal inductive coils 238, 240. The proximal and distal inductive coils 238, 240 are separated by the inter-coil gap 236, which is filled or substantially filled with the radially protruding portion of the bobbin 218. As described above, the bobbin 218 may include or be formed from a nonmagnetic and/or nonconductive material. Alternatively, one or more other nonmagnetic and/or nonconductive materials may be positioned between the proximal and distal inductive coils 238, 240. For example, one or more other polymers may be axially positioned between the proximal and distal inductive coils 238, 240.

The axial separation of the proximal and distal inductive coils 238, 240 is referred to as the separation distance 256. As shown in FIGS. 2 and 3, the separation distance 256 may span the inter-coil gap 236 and may be measured as the axial distance between opposing ends of the proximal and distal inductive coils 238, 240, or the axial distance between the radial indentations 228, 230.

The separation distance 256 is sufficiently large to prevent magnetic and/or electric coupling between the proximal and distal inductive coils 238, 240, while small enough to permit the inductive subassembly 216 to fit within relatively small lead assemblies 100, such as brady lead assemblies. For example, the separation distance 256 may be at least 40 mils (or 1.0 millimeter) but no greater than 60 mils (or 1.5 millimeters) in one embodiment. Alternatively, the separation distance 256 may be shorter than 40 mils (or 1.0 millimeter) or longer than 60 mils (or 1.5 millimeters).

Figure 6:
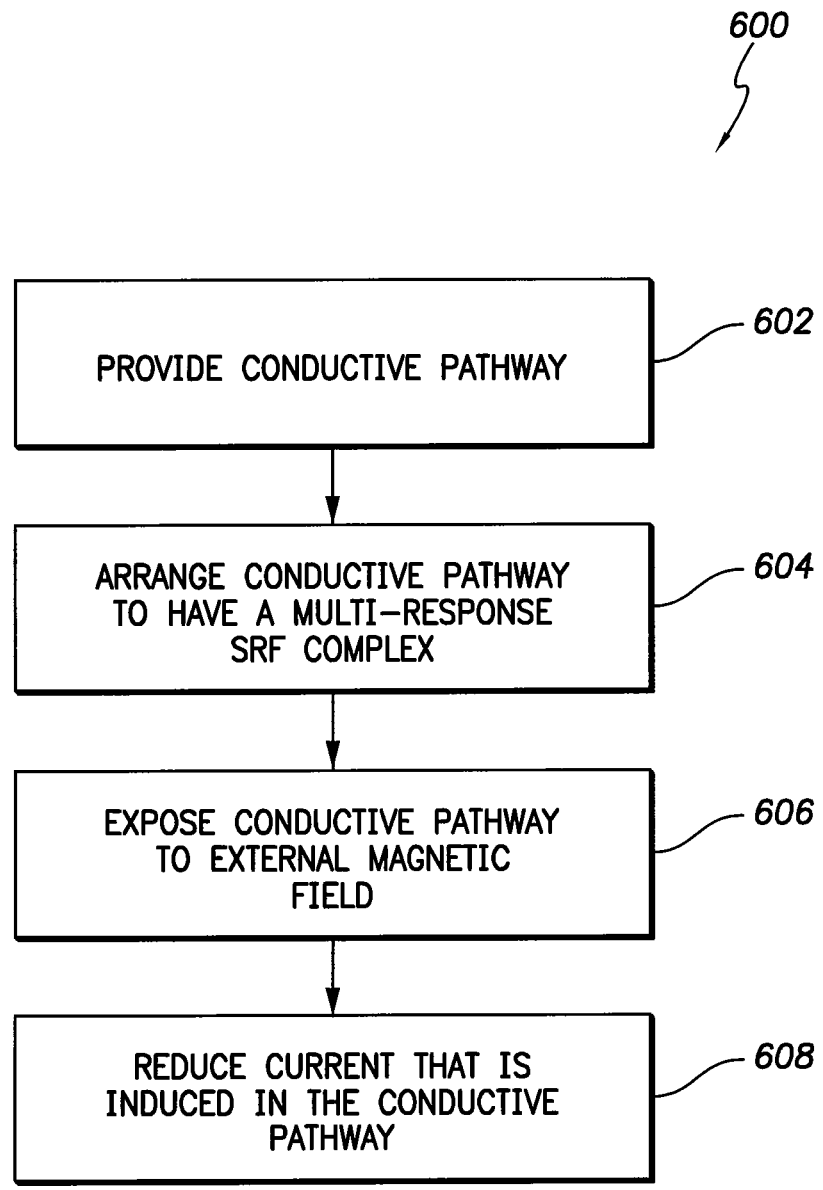
FIG. 6 is a flowchart of a method for providing a lead assembly, such as an MRI compatible lead assembly, in accordance with one embodiment.

FIG. 6 is a flowchart of a method 600 for providing a lead assembly, such as an MRI compatible lead assembly, in accordance with one embodiment. At 602, a conductive pathway, such as the fourth conductive pathway 220 (shown in FIG. 2) is provided. The conductive pathway electrically couples a medical device, such as an IMD, with one or more electrodes of the lead assembly. Electrical signals of a heart may be sensed and/or stimulus pulses may be delivered to the heart through the conductive pathway.

At 604, the conductive pathway is arranged to have a multi-response SRF complex. For example, the conductive pathway may be arranged within the lead assembly to have the multi-response SRF complex 400, 402, or 500 (shown in FIGS. 4 and 5). The conductive pathway may be arranged by wrapping the conductive pathway around the bobbin 218 (shown in FIG. 2) to form two or more inductive coils, such as the coils 238, 240 (shown in FIG. 2). Each of the coils 238, 240 may be associated with a different, separate, and distinct center frequency of the multi-response SRF complex 400, 402, 500, such as one or more of the center frequencies 434, 436, 524, 526, 528 (shown in FIGS. 4 and 5). Alternatively, the conductive pathway may be electrically coupled with an inductive component, such as an LC circuit, an RLC circuit, or another inductor, that is associated with one or more of the center frequencies 434, 436, 524, 526, 528.

One or more parameters of the conductive pathway may be varied or changed to adjust the multi-response SRF of the conductive pathway. For example, changing the thickness or gauge of the conductive pathway, the thickness and/or type of material used for the insulation surrounding the conductive pathway, the number of turns that the conductive pathway is wrapped in a coil, and/or the number of layers of turns of the conductive pathway in the coil may be varied or changed to tune or set the multi-response SRF of the conductive pathway to provide significantly larger impedance characteristics at two or more predetermined frequencies, as described above.

At 606, the conductive pathway is exposed to an external magnetic field. For example, the lead assembly and the conductive pathway may be exposed to an external magnetic field generated by an MRI system. The magnetic field may operate at a frequency that is equal or approximately equal to one or more of the center frequencies of the multi-response SRF complex of the conductive pathway.

At 608, the conductive pathway reduces or eliminates electric current that is induced in the conductive pathway by the external magnetic field. For example, when the conductive pathway is exposed to a magnetic field operating at a frequency that is equal or approximately equal to one of the center frequencies of the multi-response SRF complex, the electrical impedance characteristic of the conductive pathway may significantly increase. The increase of the impedance characteristic can reduce or eliminate the flow of magnetic field-induced electric current through the conductive pathway.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "central," "upper," "lower," "front," "rear," "distal," "proximal," and the like) are only used to simplify description of one or more embodiments described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

Although the present invention has been described with reference to preferred embodiments, persons skilled in the art will recognize that changes may be made in form and detail without departing from the spirit and scope of the invention.

What is claimed is:

1. An implantable lead assembly comprising:
    an elongated body including a distal end having an electrode and a proximal end having a header connector portion for coupling the elongated body with an implantable medical device;
    a bobbin disposed in the elongated body; and
    a conductor disposed in the elongated body and electrically coupled with the header connector portion and the electrode, the conductor wound around the bobbin to form first and second inductive coils that are axially separated from each other by an inter-coil gap formed from the bobbin, wherein the first and second inductive coils have different self resonant frequencies.

2. The lead assembly of claim 1, wherein the bobbin includes a plurality of radial indentations with each of the first and second coils of the conductor disposed in a different radial indentation.

3. The lead assembly of claim 1, wherein the bobbin radially protrudes away from a center axis of the elongated body between the first and second coils to fill the inter-coil gap.

4. The lead assembly of claim 1, wherein the bobbin is formed from a nonconductive material in the inter-coil gap.

5. The lead assembly of claim 1, wherein the bobbin is formed from a non-magnetic material in the inter-coil gap.

6. The lead assembly of claim 1, wherein the bobbin is electrically decoupled from the first and second coils of the conductor within the inter-coil gap.

7. The lead assembly of claim 1, wherein the first and second coils of the conductor are axially separated by at least 40 mils.

8. The lead assembly of claim 1, wherein the first coil of the conductor has a self resonant frequency range that includes 64 megahertz and the second coil of the conductor has a self resonant frequency range that includes 128 megahertz.

9. The lead assembly of claim 1, wherein the first coil of the conductor includes a greater number of turns around a center axis of the elongated body than the second coil of the conductor.

10. The lead assembly of claim 1, wherein the first and second coils of the conductor include the same number of layers of turns around a center axis of the elongated body.

11. An implantable lead assembly comprising:
    an elongated body including a distal end having an electrode and a proximal end having a header connector portion configured to be coupled with an implantable medical device;
    a bobbin disposed in the elongated body, the bobbin including radial indentations that are axially separated from each other by an inter-coil gap; and
    a conductor extending through the elongated body and electrically coupled with the header connector portion and the electrode, the conductor wound around the bobbin in the radial indentations to form first and second inductive coils having different self resonant frequencies and separated from each other by the inter-coil gap.

12. The lead assembly of claim 11, wherein the bobbin radially protrudes away from a center axis of the elongated body between the first and second coils to fill the inter-coil gap.

13. The lead assembly of claim 11, wherein the inter-coil gap is substantially filled with a nonconductive and nonmagnetic material of the bobbin.

14. The lead assembly of claim 13, wherein the nonconductive and nonmagnetic material of the bobbin in the inter-coil gap axially extends from the first coil to the second coil of the conductor.

15. The lead assembly of claim 11, wherein the first and second coils of the conductor are axially separated by 60 mils or less.

16. The lead assembly of claim 11, wherein the first coil of the conductor has a self resonant frequency range that includes 64 megahertz and the second coil of the conductor has a self resonant frequency range that includes 128 megahertz.

17. The lead assembly of claim 11, wherein winding configurations of the first and second coils of the conductor differ from each other.

18. The lead assembly of claim 17, wherein the first coil of the conductor includes a greater number of turns around a center axis of the elongated body than the second coil of the conductor.

19. The lead assembly of claim 18, wherein the first and second coils of the conductor include the same number of layers of turns around a center axis of the elongated body.

\* \* \* \* \*